US008696680B2

(12) United States Patent
Iannotti et al.

(10) Patent No.: US 8,696,680 B2
(45) Date of Patent: Apr. 15, 2014

(54) METHOD AND APPARATUS FOR INSERTION OF AN ELONGATE PIN INTO A SURFACE

(75) Inventors: Joseph P. Iannotti, Cleveland, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 183 days.

(21) Appl. No.: 13/306,083

(22) Filed: Nov. 29, 2011

(65) Prior Publication Data

US 2012/0136365 A1    May 31, 2012

Related U.S. Application Data

(63) Continuation-in-part of application No. 12/854,362, filed on Aug. 11, 2010, now abandoned.

(60) Provisional application No. 61/232,842, filed on Aug. 11, 2009.

(51) Int. Cl.
*A61B 17/58* (2006.01)
*A61B 17/60* (2006.01)
*A61F 2/00* (2006.01)

(52) U.S. Cl.
USPC .................................... 606/96; 606/104

(58) Field of Classification Search
USPC ...................... 606/96–98, 103, 104
See application file for complete search history.

(56) References Cited

U.S. PATENT DOCUMENTS

| | | | |
|---|---|---|---|
| 2,181,746 A * | 11/1939 | Siebrandt | 606/96 |
| 4,834,080 A | 5/1989 | Brown | |
| 5,047,061 A | 9/1991 | Brown | |
| 5,133,720 A | 7/1992 | Greenberg | |
| 5,403,322 A | 4/1995 | Herzenberg et al. | |
| 5,437,677 A | 8/1995 | Shearer et al. | |
| 5,769,856 A | 6/1998 | Dong et al. | |
| 5,833,693 A | 11/1998 | Abrahami | |
| 5,980,526 A | 11/1999 | Johnson et al. | |
| 6,254,606 B1 | 7/2001 | Carney et al. | |
| 6,273,891 B1 | 8/2001 | Masini | |
| 6,342,056 B1 | 1/2002 | Mac-Thiong et al. | |
| 6,387,100 B1 | 5/2002 | Lindequist | |
| 6,494,913 B1 | 12/2002 | Huebner | |
| 6,752,812 B1 | 6/2004 | Truwit | |
| 6,821,300 B2 | 11/2004 | Masini | |
| 7,153,309 B2 | 12/2006 | Huebner et al. | |
| 7,229,478 B2 | 6/2007 | Masini | |

(Continued)

*Primary Examiner* — Andrew Yang
*Assistant Examiner* — Olivia C Chang
(74) *Attorney, Agent, or Firm* — Tarolli, Sundheim, Covell & Tummino LLP (57) ABSTRACT

A trajectory structure is configured for contact with a surface to dictate an insertion trajectory of a pin relative to the surface. A location structure is configured to allow longitudinal passage of at least a portion of the pin therethrough to dictate an insertion location of the pin relative to the surface. An elongate handling rod is connected to the trajectory structure and the location structure. The handling rod supports the trajectory structure and the location structure for manipulation by a user. The handling rod spaces the trajectory structure and the location structure longitudinally apart. The trajectory structure is connected to the handling rod for trajectory adjustment in at least two degrees of freedom relative to the handling rod. The insertion trajectory of the pin insertion is substantially dependent upon the trajectory adjustment. A method for inserting an elongate guide pin into a bone surface is also provided.

15 Claims, 10 Drawing Sheets

(56) References Cited

U.S. PATENT DOCUMENTS

| | | |
|---|---|---|
| 7,294,133 B2 | 11/2007 | Zink et al. |
| 7,297,163 B2 | 11/2007 | Huebner |
| 7,364,581 B2 | 4/2008 | Michalowicz |
| 2002/0133172 A1 | 9/2002 | Lambrecht et al. |
| 2003/0149486 A1 | 8/2003 | Huebner |
| 2005/0119561 A1 | 6/2005 | Kienzle, III |
| 2005/0234472 A1 | 10/2005 | Huebner |
| 2007/0027417 A1 | 2/2007 | Chudik |
| 2007/0100353 A1 | 5/2007 | Chudik |
| 2007/0250174 A1 | 10/2007 | Tornier et al. |
| 2007/0276401 A1 | 11/2007 | Choe et al. |
| 2008/0114369 A1 | 5/2008 | Bastian |
| 2008/0183191 A1 | 7/2008 | Schoepp |
| 2008/0215057 A1* | 9/2008 | Willi et al. ............ 606/88 |

* cited by examiner

METHOD AND APPARATUS FOR INSERTION OF AN ELONGATE PIN INTO A SURFACE

RELATED APPLICATIONS

This application is a continuation-in-part of U.S. patent application Ser. No. 12/854,362, filed Aug. 11, 2010 now abandoned, which claims benefit of U.S. Provisional Patent Application Ser. No. 61/232,842, filed Aug. 11, 2009, the subject matter of both of which is incorporated herein by reference.

TECHNICAL FIELD

The present invention relates to an apparatus and method for use of an insertion tool and, more particularly, to an apparatus for dictating trajectory and location for insertion of an elongate pin into a surface.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault.

Because the shoulder prosthesis is normally provided to correct a congenital or acquired defect of the native shoulder joint, the glenoid vault often exhibits a pathologic, nonstandard anatomic configuration. A surgeon must compensate for such pathologic glenoid vault anatomy when implanting the glenoid component in striving to achieve a solid anchoring of the glenoid component into the glenoid vault. Detailed preoperative planning, using two- or three-dimensional internal images of the shoulder joint, often assists the surgeon in compensating for the patient's anatomical limitations. During the surgery, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin may be temporarily or permanently placed into the exposed bone surface to help orient the surgeon and thereby enhance the accuracy and efficiency of the surgical procedure.

A carefully placed guide pin, regardless of the reason provided, will reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, an apparatus for dictating trajectory and location for insertion of an elongate pin into a surface is described. A trajectory structure is configured for contact with the surface to dictate an insertion trajectory of the pin relative to the surface. A location structure is configured to allow longitudinal passage of at least a portion of the pin therethrough to dictate an insertion location of the pin relative to the surface. An elongate handling rod is connected to the trajectory structure and the location structure. The handling rod supports the trajectory structure and the location structure for manipulation by a user. The handling rod spaces the trajectory structure and the location structure longitudinally apart. The trajectory structure is connected to the handling rod for trajectory adjustment in at least two degrees of freedom relative to the handling rod. The insertion trajectory of the pin insertion is substantially dependent upon the trajectory adjustment.

In an embodiment of the present invention, a method for inserting an elongate guide pin into a bone surface is described. A trajectory structure adjustable in at least three degrees of freedom relative to the bone surface is provided. A location structure connected to and longitudinally spaced from the trajectory structure is provided. An insertion trajectory of the guide pin relative to the bone surface is dictated by maintaining the trajectory structure in a predetermined position defined by at least two degrees of freedom relative to the bone surface. The bone surface is contacted with the trajectory structure. An insertion location of the guide pin relative to the bone surface is dictated by passing at least a distal end of the guide pin longitudinally through the location structure. The bone surface is contacted with the distal end of the guide pin at the insertion location. The distal end of the guide pin is inserted into the bone surface along the insertion trajectory.

BRIEF DESCRIPTION OF THE DRAWINGS

For a better understanding of the invention, reference may be made to the accompanying drawings, in which.

DESCRIPTION OF EMBODIMENTS

Figures 1A, 1B:
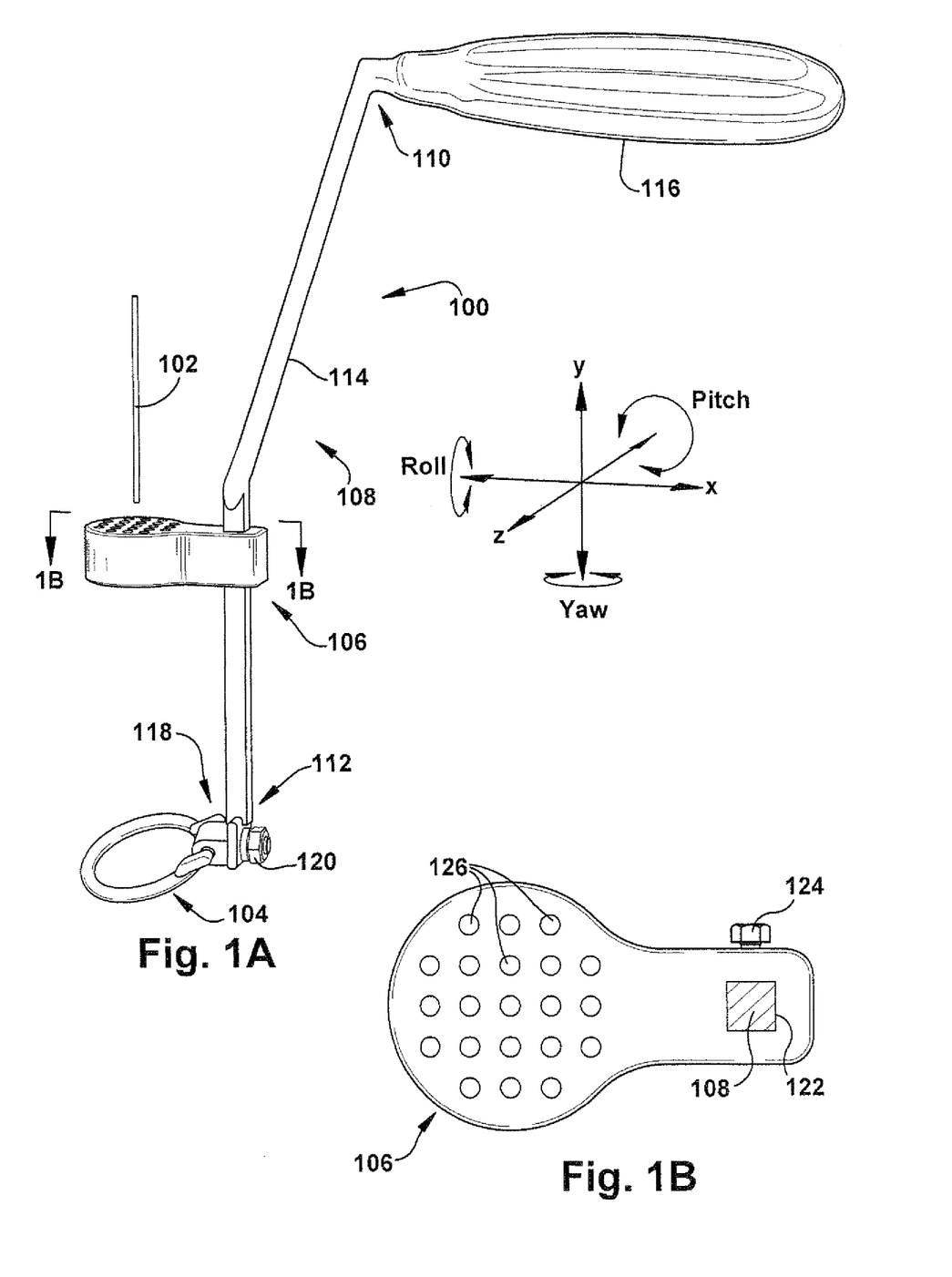
FIG. 1A is a side view of one embodiment of the present invention in a first configuration.
FIG. 1B is a cross-sectional view taken along line B-B of FIG. 1A.

In accordance with the present invention, FIG. 1A depicts an apparatus 100, such as a guide pin positioning apparatus, for dictating trajectory and location for insertion of an elongate pin (schematically shown at 102) into a surface. The term "dictate" is defined herein as "requiring or determining necessarily".

A trajectory structure 104 is configured for selective contact with the surface to dictate an insertion trajectory of the pin 102 relative to the surface. A location structure 106 is configured to allow longitudinal passage of at least a portion of the pin 102 therethrough to dictate an insertion location of the pin relative to the surface. At least a portion of each of the location structure 106 and the trajectory structure 104 may be at least one of a block, a ring, a paddle, a yoke, a saddle, a dome, and a dish. For example, the trajectory structure 104 shown in FIG. 1A includes a ring-shaped portion, and the location structure 106 shown in FIG. 1A includes a paddle-shaped portion. In certain applications of the present invention, the ring-shaped portion of the trajectory structure 104 may be sufficient to locate the pin 102 relative to the surface, and thus a separate location structure 106 need not be provided.

Since directions and orientations are used throughout this description, a three-dimensional coordinate system has been placed in FIG. 1A to clarify the references made herein. The "longitudinal" direction substantially corresponds to the Y-axis shown. A direction "lateral" to the Y-axis will lie in the plane defined by the X- and Z-axes, where the Z-axis extends into and out of the XY-plane (here coincident with the plane of FIG. 1A). "Degrees of freedom" refers herein to any of a limited number of ways in which a body may move or in which a dynamic system may change. The coordinate system of FIG. 1A defines six degrees of freedom:

1. Proximal and distal translation along the Y-axis ("longitudinal")
2. Rotation about the Y-axis ("yaw")
3. Back and forth translation along the X-axis ("lateral" to Y-axis)
4. Rotation about the X-axis ("roll")
5. In and out translation along the Z-axis ("lateral" to Y-axis)
6. Rotation about the Z-axis ("pitch")

Motion described herein with reference to one or more of these degrees of freedom should be understood to be substantially in accordance with the indicated degree of freedom, but does not necessarily denote strict and absolute adherence to the directional motion indicated. For example, a bone surface may have an uneven surface contour and so might not, as a whole, lie entirely within an XZ-plane even if the bone surface is described as extending "laterally". One of ordinary skill in the art will recognize that directional terms are used herein for ease of description and may permit some amount of approximation in understanding the construction and use of the apparatus 100.

An elongate handling rod 108 is connected to the trajectory structure 104 and the location structure 106, and spaces the trajectory and location structures longitudinally apart. The handling rod 108 may have proximal and distal handling rod ends 110 and 112, respectively, longitudinally spaced by a handling rod body 114. The handling rod 108 supports the trajectory structure 104 and the location structure 106 for manipulation by a user and accordingly the proximal handling rod end 110 may include a handle 116, such as that shown in FIG. 1A, to facilitate grasping by the user for manipulation of the apparatus 100 relative to the surface. The user is thus able to manipulate the apparatus 100 shown in FIG. 1A in all six degrees of freedom relative to any other structure, such as the surface, except as restricted by contact with that structure, as will be discussed below.

The trajectory structure 104 is connected to the distal handling rod end 112 and is adjustable in at least two degrees of freedom relative to the handling rod 108 to dictate the insertion trajectory of the pin 102 into the surface. For example, and as shown in FIG. 1A, the trajectory structure 104 could be connected to the distal handling rod end 112 by a wristed joint 118 which allows the trajectory structure to be manipulated relative to the handling rod 108 and then held in the desired position through tightening of at least one set screw 120. One of ordinary skill in the art can readily provide a suitable wristed joint 118 or other manipulable structure which allows the trajectory structure 104 to be adjusted to, and permanently or reversibly held in, a position relative to the handling rod 108 to dictate a predetermined insertion trajectory. For example, the wristed joint 118 shown in FIG. 1A permits adjustment of the trajectory structure 104 relative to the handling rod 108 in at least the pitch and roll directions. The wristed joint 118 or other manipulable structure may be a single joint (such as a universal or ball joint) or a combination of joints (such as a series of hinge joints). The insertion trajectory of the pin 102 may be substantially dependent upon the trajectory adjustment of the trajectory structure 104.

As depicted in FIG. 1A, the location structure 106 is connected to the handling rod body 114 at a location longitudinally spaced apart from the trajectory structure 104. The location structure 106 may be longitudinally adjustable along the handling rod body 114 with respect to the trajectory structure 104. For example, and as shown in FIG. 1B, the handling rod 108 could extend through a rod aperture 122 in the location structure 106, and a set screw 124 could be tightened to exert force upon the handling rod and maintain the relative longitudinal position of the location structure upon the handling rod.

The location structure 106 may include a plurality of laterally spaced location apertures 126 extending therethrough, as shown in the cross-sectional view of FIG. 1B. When location apertures 126 are provided, the insertion location may be at least partially dictated by the location aperture chosen for passage of at least a portion of the pin 102 therethrough. For example, the location apertures 126 could be provided in a grid arrangement, as shown, having known grid spacing (e.g., 1 mm center-to-center spacing in both the X-axis and Z-axis directions). The user can then select a particular location aperture 126 for insertion of the pin 102 based at least partially upon a desired distance of the insertion location from another structure of the apparatus 100, such as the handling rod 108.

The location structure 106 may have any desired Y-axis thickness. However, and with reference to FIG. 1A, it may be desirable for the thickness of the location structure 106 to be sufficient to substantially prevent toggling (that is, rotation in the pitch and/or roll directions) of the pin 102 within the location aperture 126 during insertion of the pin.

It is contemplated that the location aperture(s) 126 will extend completely through the thickness of the location structure 106 to allow passage of the pin 102, and that the location aperture(s) 126 will have a slightly larger diameter than that of the largest pin likely to be used with the apparatus 100. Additionally, in particular applications of the apparatus 100, the user will remove the apparatus 100 longitudinally after insertion of the pin, and the location aperture 126 will slide proximally over a "head" end of the pin; in such case, the location aperture(s) 126 should have a slightly larger dimension than that of any lateral portion of the largest pin likely to be used with the apparatus 100.

It is also contemplated that the location structure 106 may be configured to allow longitudinal passage of at least a portion of a pilot drill (not shown) therethrough. A pilot drill may be useful in preparing the surface for secure insertion of a pin 102. For example, the drill bit of the pilot drill might be used to drill a pilot hole into the surface, the pilot hole having the same insertion location and trajectory as that desired for the later-inserted pin 102. Similarly to the insertion of a pin 102 having no pre-drilled pilot hole, the location structure 106 will dictate an insertion location of the pilot drill with respect to the surface and the trajectory structure will dictate an insertion trajectory of the pilot drill with respect to the surface.

A depth control feature (not shown) may be provided to the apparatus 100 to indicate and/or limit a depth to which the pin 102 is inserted into the surface. For example, the handling rod 108 could be provided with a series of longitudinally spaced indicator marks to convey to the user the spacing of a particular portion of the pin 102 from the distal handling rod end 112, a dial-type indicator could be moved by insertion of the pin 102 past a metering wheel, or a clamshell-type spacer block could be located atop or around the location structure 106 and block a laterally expanded (e.g., head-type) portion of the pin from moving distally past an imposed border spaced longitudinally apart from the location structure. The pin 102 could also or instead be marked with an insertion distance indication scale such as, but not limited to, hash marks, numbers, color bands, radiopaque markers, or the like.

During preoperative or intraoperative planning, a user of the apparatus 100 can choose an appropriate insertion trajectory and insertion location for the pin 102 with respect to the surface. The insertion trajectory and/or location may be selected based upon the user's professional knowledge and expertise, optionally supplemented with reference to multi-dimensional images of the surface. For example, the user may consult computer tomography ("CT") data of the surgical site including the surface. Additionally or alternatively, the insertion trajectory and/or location may be selected through consultation of patient scans using digital or analog radiography, magnetic resonance imaging, or any other suitable imaging means. The surgical site scan data is optionally displayed for the user to review and manipulate, such as through the use of a computer or other graphical workstation interface. The selection of the insertion trajectory and/or location is described as being performed on three-dimensional models; however, one or more two-dimensional depictions of the surgical site may also or instead be consulted during preoperative and/or interoperative planning.

Once a final desired pin 102 position has been determined, optionally with the assistance of multi-dimensional imaging technology, the desired insertion location and trajectory can be determined. The trajectory structure 104 and/or location structure 106 can then be adjusted relative to the handling rod 108 to dictate the insertion trajectory and location, respectively. This adjustment can be accomplished manually, as will be described below, or automatically, through the use of a setting jig or other tool (such as, but not limited to, those disclosed in co-pending U.S. Provisional Patent Application No. 61/534,142, filed 13 Sep. 2011 and titled "Apparatus and Method for Transferring Predetermined Spatial Positioning Information to an Adjustable Tool", the entire contents of which are incorporated herein by reference), or through fabrication of a single-use, non-adjustable apparatus 100 corresponding to the desired insertion trajectory and location.

The location structure 106 shown in FIG. 1A may be adjusted longitudinally with respect to the handling rod 108, if desired. However, one of ordinary skill in the art will recognize that the position of the location structure 106 is less related to the insertion location than is the choice of location aperture 126 or other portion of the location structure through which the pin 102 is passed. Nonetheless, perhaps to accommodate spatial conditions at or near the surface, or to avoid interference with other structures or tools used in the surgery (e.g., retractors, imaging tools, or the pin 102), the location structure 106 may be movable relative to the handling rod 108. For example, and as shown in FIG. 1B, the set screw 124 may be loosened by hand or with a manipulating tool, the location structure 106 may be moved longitudinally along the handling rod body 114 to a desired position, then the set screw may be re-tightened to maintain that set position of the location structure. Optionally, the location structure 106 can be moved longitudinally while a portion of the pin 102 is still extending through the location structure, such as when the user disengages the apparatus 100 from the inserted pin for removal of the apparatus from the surface.

Figure 2:
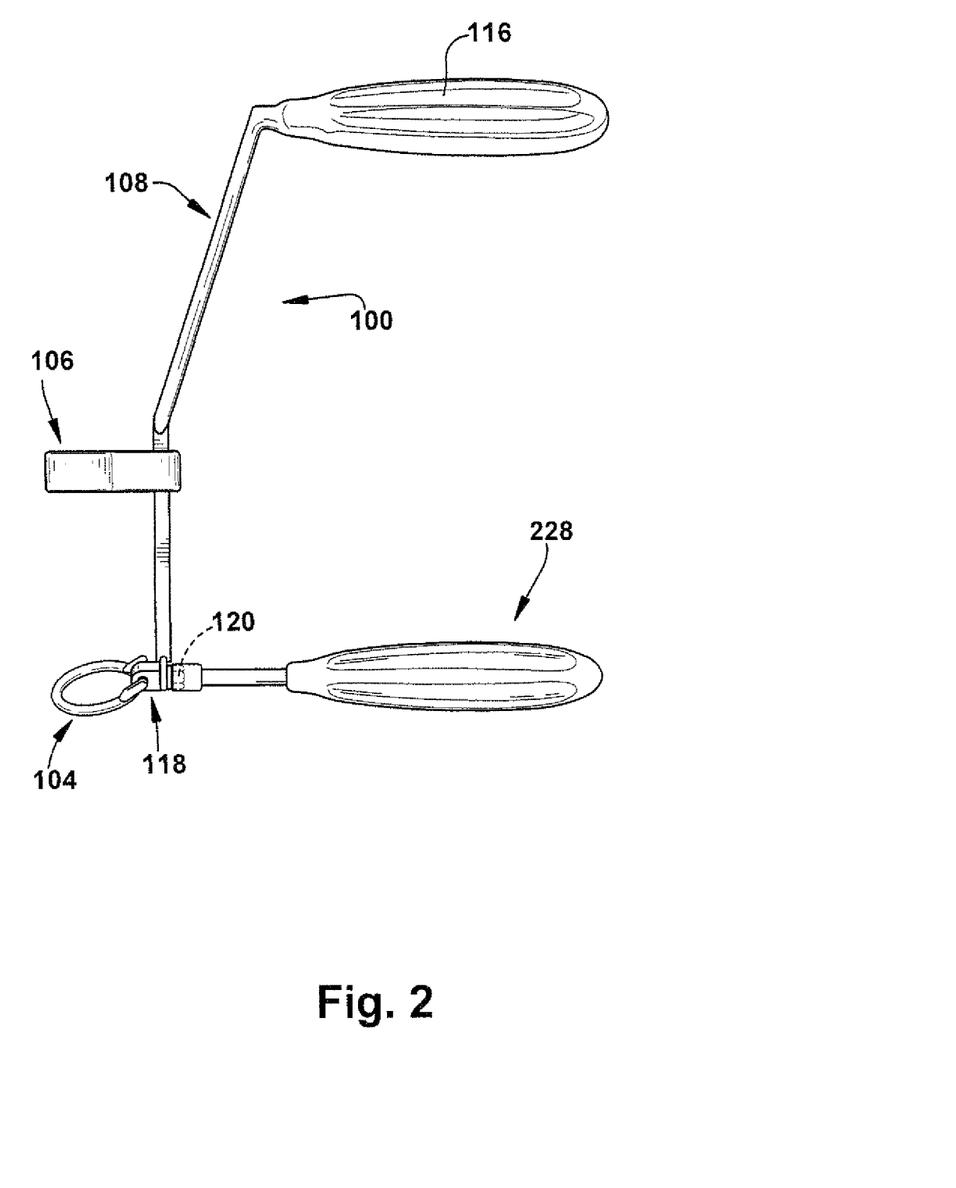
FIG. 2 is a side view of the embodiment of FIG. 1A during a change of configuration.

Adjustment of the trajectory structure 104 is more complicated than for the location structure 106, due to the availability of more degrees of freedom for the trajectory structure relative to the handling rod 108. As shown in FIG. 2, an adjustment aid tool 228 may be provided to interact with the apparatus 100 and facilitate dictation of at least one of the insertion trajectory and the insertion location. For example, the adjustment aid tool 228 could act as the aforementioned manipulating tool and interact with the set screw 124 during adjustment of the location structure 106. As another example, and as shown in FIG. 2, the adjustment aid tool 228 could interact with the set screw 120 during adjustment of the trajectory structure. The adjustment aid tool 228 may be an Allen wrench, Philips screwdriver, slotted screwdriver, TORX™ wrench, Robertson wrench, outside hex wrench, inside hex wrench, or any other adjustment aid tool or combination thereof suitable for interaction with the apparatus 100.

Figure 3:
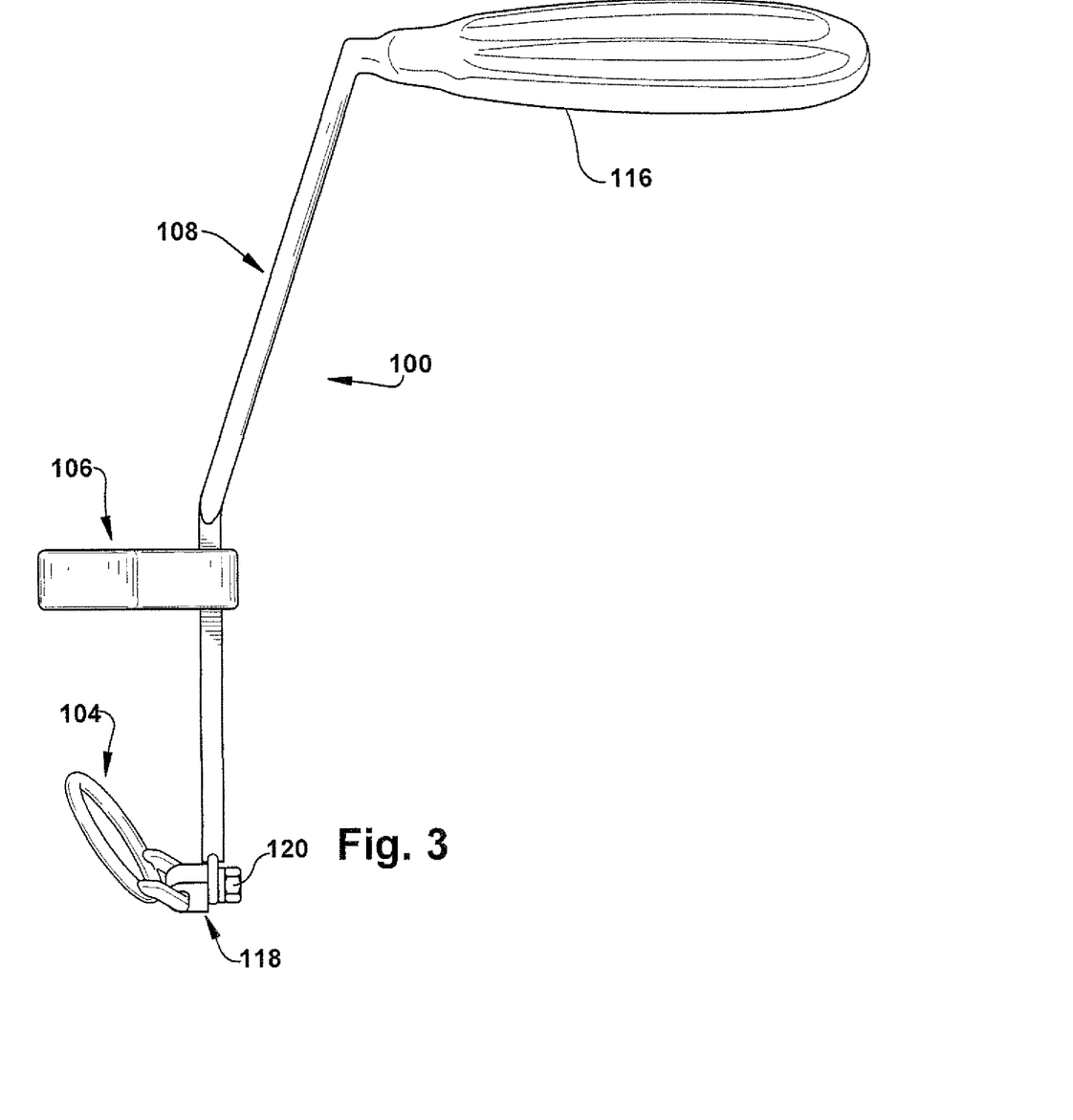
FIG. 3 is a side view of the embodiment of FIG. 1A in a second configuration.

Regardless of the manner in which the trajectory structure 104 is released for adjustment and then secured into place, the trajectory structure may be preoperatively and/or intraoperatively adjusted to facilitate insertion of the pin 102 into the surface along the insertion trajectory. An example of this adjustment is shown as the apparatus 100 changes from the first configuration of FIG. 1A to the second configuration of FIG. 3. In FIG. 1A, the trajectory structure 104 is oriented largely within the XZ-plane, lateral to the Y-axis. The configuration of the apparatus 100 is then changed, optionally using the adjustment aid tool 228 shown in FIG. 2, until the trajectory structure 104 reaches the second configuration of FIG. 3. The trajectory structure 104 shown in FIG. 3 has been rotated in the "pitch" direction from the FIG. 1A first configuration.

The amount and direction of movement of the trajectory structure 104 during adjustment will be determined by the user, who can then manipulate the trajectory structure into the desired position. In certain implementations of the present invention, the relationship and mechanical connection between the handling rod 108 and the trajectory structure 104 will be such that the angle therebetween directly corresponds to the insertion trajectory. The apparatus 100 shown in the Figures exhibits such direct correspondence, at least for the portion of the handling rod 108 to which the trajectory structure 104 is connected. It should be noted that the proximal handling rod end 110 angles away from the distal handling rod end 112 in the manner shown to allow user visualization of the location structure 106 and trajectory structure 104 during use, and this angling-away does not limit the relative positions described herein for the handling rod 108.

Optionally, a positioning aid (not shown), such as, but not limited to, a protractor-based angle-setting device or a custom angling block/jig produced using patient imaging data, may assist the user in quickly and accurately setting the trajectory structure 104 to dictate the desired insertion trajectory. Examples of suitable positioning aids are provided in the aforementioned U.S. Provisional Patent Application No. 61/534,142 and in co-pending U.S. Provisional Patent Application No. 61/408,392, filed 29 Oct. 2010 and titled "System of Preoperative Planning and Provision of Patient-Specific Surgical Aids", the entire contents of which are incorporated herein by reference. Another example of a possible positioning aid is at least one detent feature (not shown) configured to facilitate discrete manual adjustment of the trajectory structure 104 relative to the handling rod 108 in at least one degree of freedom. The detent feature could be a toothed wheel providing a ratchet-type arrangement in the pitch movement direction of the wristed joint 118, for example. Depending upon the size of the apparatus 100, a numerical scale (not shown) could even be provided for repeatable adjustment of the wristed joint 118 into discrete positions. For example, a particular insertion trajectory could correspond to some single combination of possible discrete positions 1-10 in each of the pitch and roll directions. However, an experienced user may be able to manually set the trajectory structure 104 into a position to sufficiently dictate the desired insertion trajectory without assistance of a positioning aid.

A scapula 430 is shown and described with reference to FIGS. 4-6 as an example use environment, and the surface 432 is discussed herein as a bone surface (more specifically, a glenoid vault surface). The surface 432 may, however, be any suitable surface, including, but not limited to, a body tissue surface or any other surface in a medical or non-medical context into which a pin is to be inserted at a predetermined insertion location and/or trajectory. A method of inserting a pin 102 into the surface 432 includes dictating the insertion trajectory and location through use of the apparatus 100. The location structure 106 and trajectory structure 104 shown in FIGS. 4-6 are presumed to have already been placed in appropriate positions in the manner previously described, optionally with reference to preoperative images of the scapula 430.

The apparatus 100 is then moved within the six degrees of freedom of FIG. 1A—for example, in the X-axis, Y-axis, and yaw directions, or any other combination of degrees of freedom—until the trajectory structure 104 contacts the surface 432. The trajectory structure 104 could noninvasively contact the surface 432 or may include one or more anchoring spikes (not shown) or other means for invasively engaging the surface. As shown in FIG. 4, the trajectory structure 104 may contact an area of the surface 432 of the scapula 430 adjacent the final insertion position (shown as dashed line 434 and corresponding to the dictated insertion trajectory and location) of the pin. The term "adjacent" is used here to indicate two locations nearby, or in close proximity, to one another. Optionally, the apparatus 100 as a whole may only contact an area of the surface 432 of the scapula 430 adjacent the insertion position, with no portions of the apparatus contacting, for example, a portion of the scapula surface located outside the glenoid vault.

Figure 4:
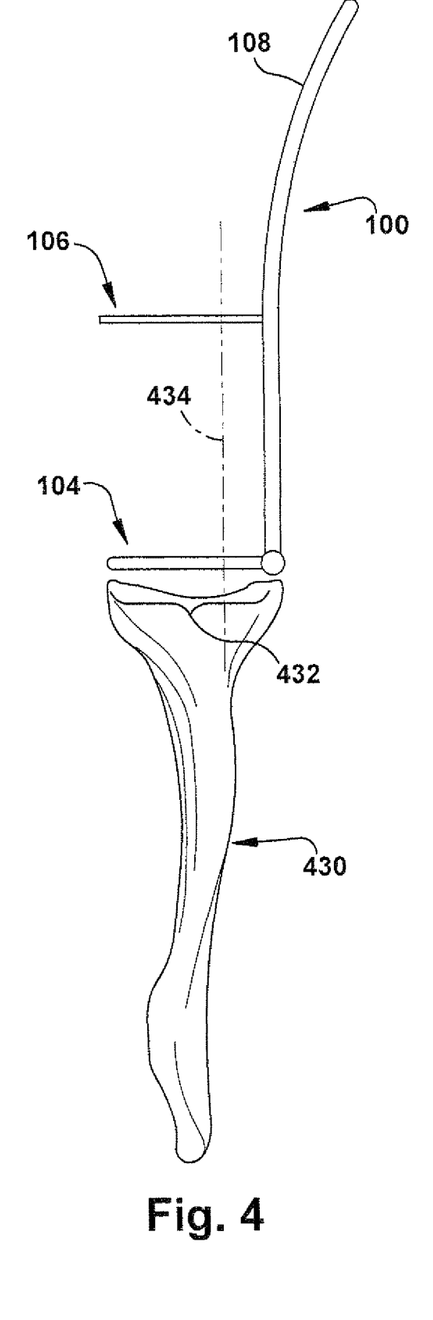
FIG. 4 is a schematic side view of the embodiment of FIG. 1A in a first configuration in a first use environment.
Figure 5:
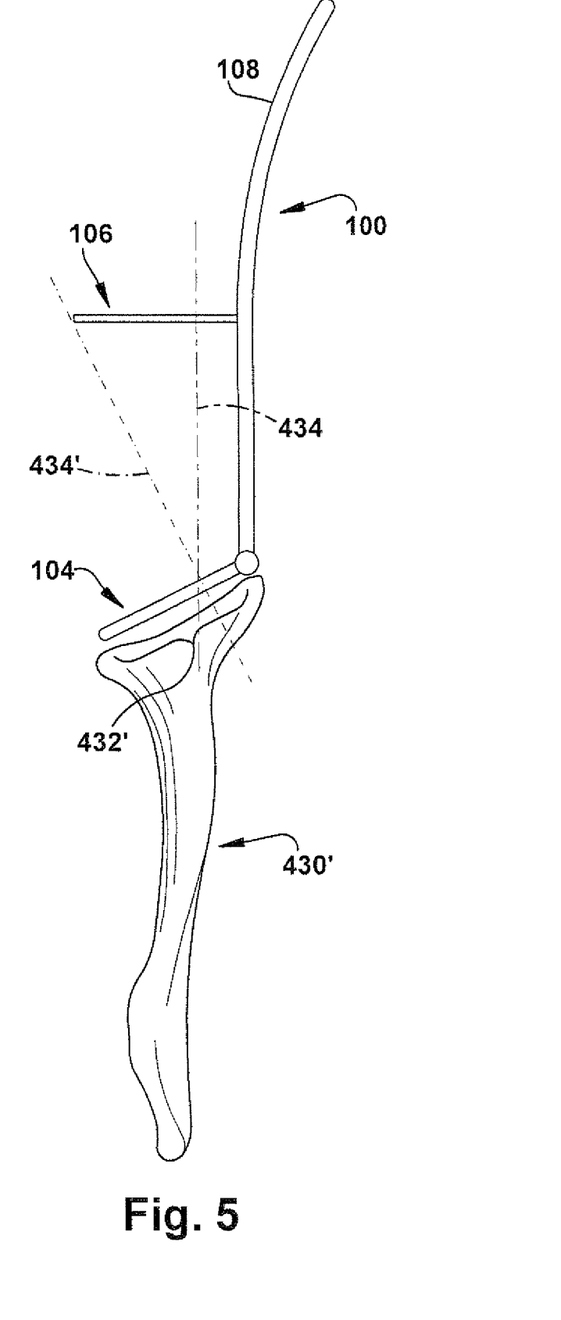
FIG. 5 is a schematic side view of the embodiment of FIG. 1A in a second configuration in a second use environment.
Figure 6:
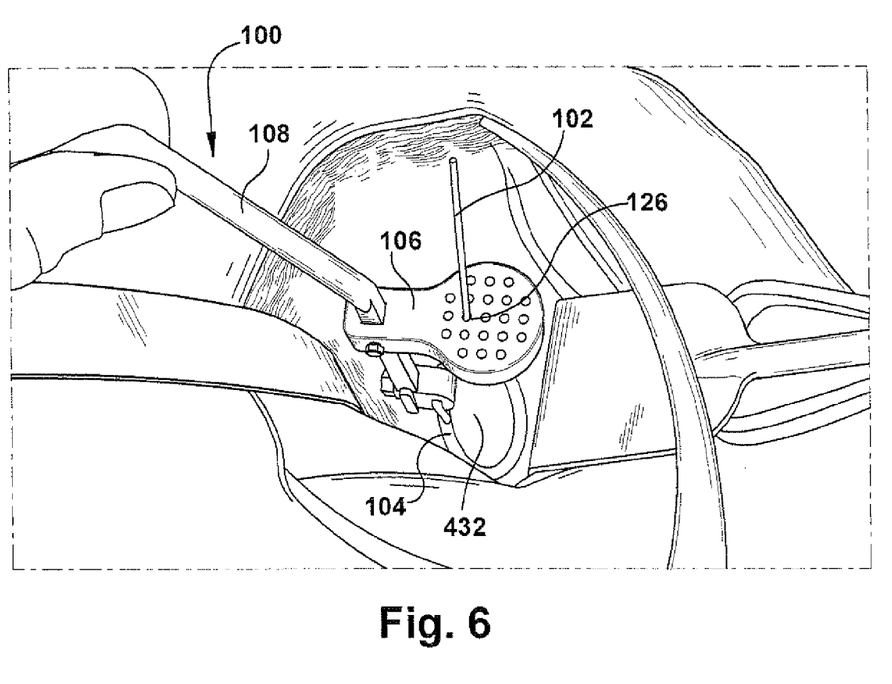
FIG. 6 is a top perspective view of the embodiment of FIG. 1A in a third use environment.

Once the apparatus 100 has been placed in the relationship with the surface 432 shown in FIGS. 4-6 for the first, second, and third use environments, respectively, depicted therein, a distal end of a pin is moved longitudinally through the location structure, and optionally through a location aperture 126 (when provided) thereof. The distal end of the pin then is brought into contact with the surface 432 at the insertion location and sufficient force is exerted upon the pin to insert the distal end of the pin into the surface along the insertion trajectory, up to a desired insertion depth, which may be predetermined. When the pin has been placed into the insertion position and to the insertion depth, the apparatus 100 is removed from the surface 432 and the surgical procedure can proceed as desired, with the pin protruding from the surface 432 to serve as a fixed landmark.

FIGS. 4 and 5 schematically depict the apparatus 100 in relation to bone surfaces of two anatomically different scapulae 430 and 430', respectively. In FIG. 4, the insertion trajectory and location have been dictated to allow approximately perpendicular placement of the pin into the surface 432 of the glenoid vault, while allowing the pin to penetrate into a portion of the scapula 430 which is sufficiently thick to provide stable support of the inserted pin, as shown by insertion position 434. In FIG. 5, conversely, insertion of a pin into the surface 432' at an approximately perpendicular angle would result in an insertion position (shown in dash-dot line at 434') which undesirably protrudes from a spaced-apart, "underside" location on the scapula 430' due to an unusual glenoid vault angle of that scapula. The user in the second use embodiment of FIG. 5 would be aware of the unusual angling of the scapula 430' due to preoperative imaging, and could therefore choose an insertion trajectory and location which compensatorily provides an insertion position 434 into a stably supporting area of the scapula 430', as shown in dashed line.

FIG. 6 depicts a top view of a pin 102 extending through a selected location aperture 126 of the location structure 106 and into the surface 432. As is shown in FIG. 6, the user may have little to no direct intraoperative view of areas of the surface 432 other than those adjacent the insertion location, and thus the apparatus 100 may be helpful to the user in quickly and accurately placing the pin 102 according to preoperative imaging data and planning.

Figure 7:
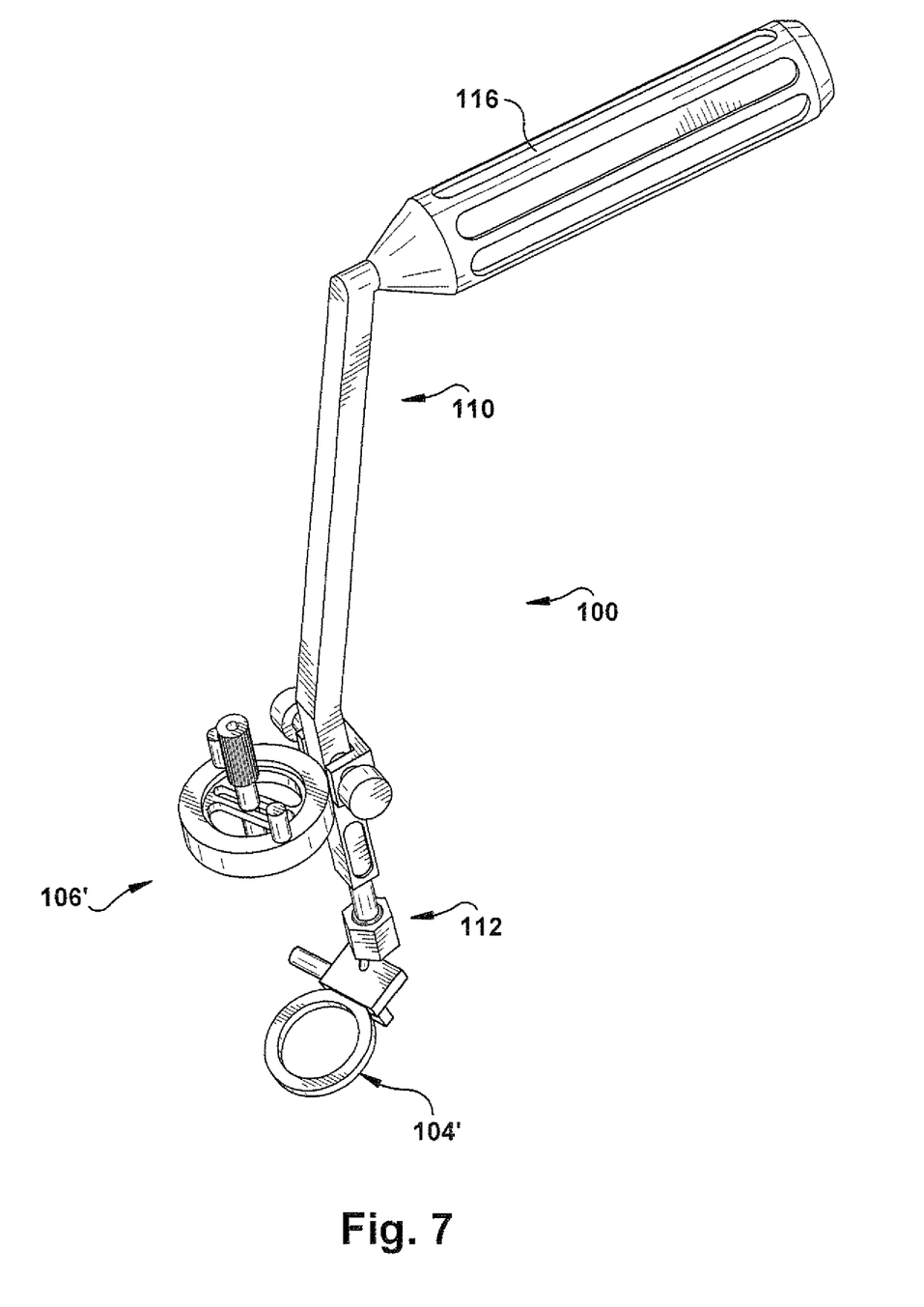
FIG. 7 is a partial top perspective view of the embodiment of FIG. 1A in an optional configuration.

FIG. 7 is a top perspective view of the apparatus 100 having optional configurations of the trajectory structure 104' and the location structure 106' which differ from those shown in the embodiment of FIG. 1A. The trajectory structure 104' and 106' of FIG. 7 are shown in magnified view in FIGS. 8-11.

Figure 8:
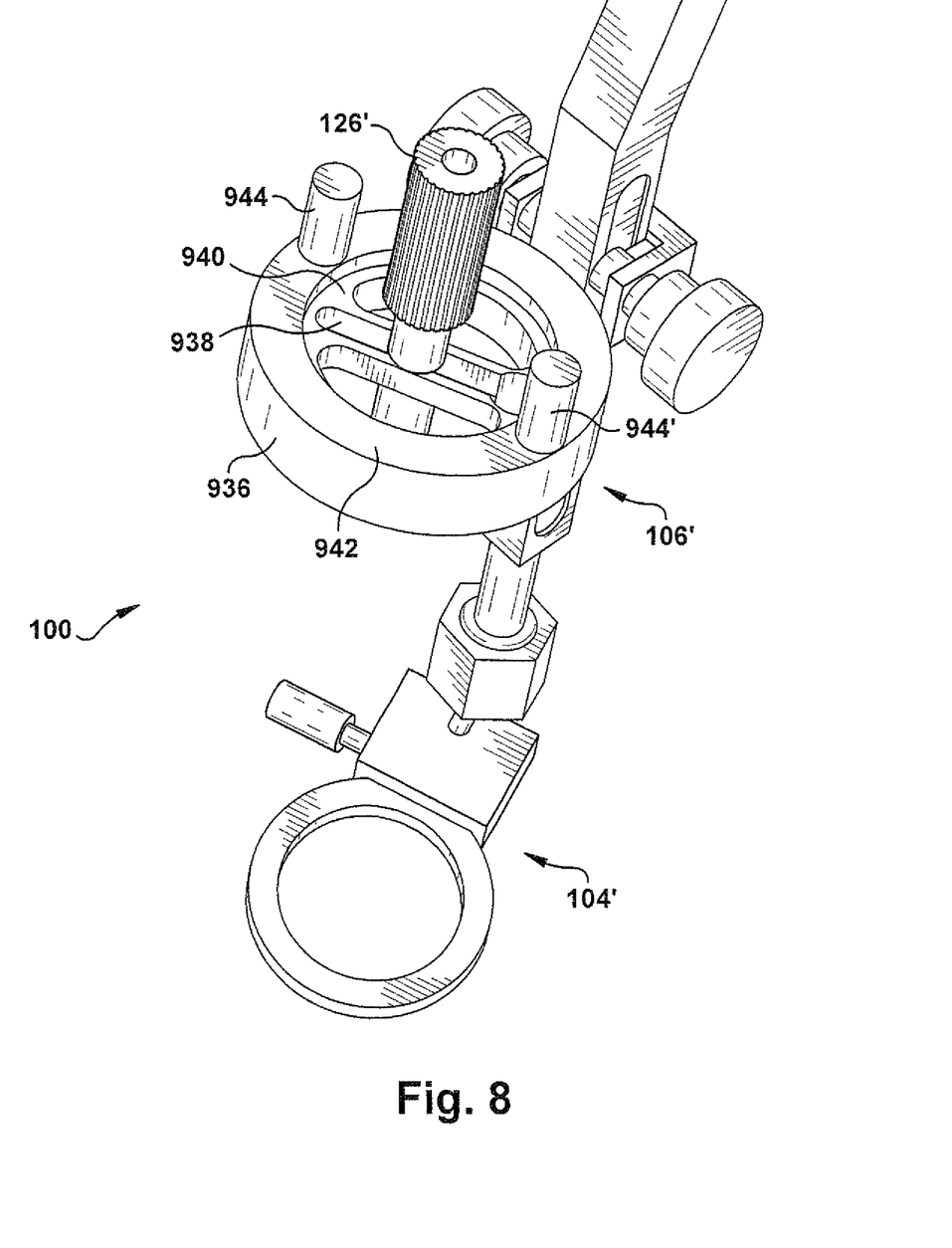
FIG. 8 is a partial top perspective view of the embodiment of FIG. 7.

As shown in FIG. 8, the location structure 106 includes an adjustable location aperture 126' which is substantially infinitely movable within a location ring 936. Here, the location aperture 126' is an elongate cylinder having a bore through which a pin 102 can be passed; the elongation of the cylinder may help to prevent precessing or toggling of the pin with respect to the location ring 936. The location aperture 126' cylinder can be moved back and forth (laterally) along a lateral slot 938, and the location structure 106 may include some provision (not shown) for detent or affixation of the location aperture 126' at a desired location with respect to the lateral slot 938.

The location aperture 126' may, also or instead of being laterally movable with respect to the lateral slot 938, be rotatable within the location ring 936. For example, the location aperture 126' could be carried by a rotation disk 940 which is adapted for rotary motion with respect to at least one stationary disk 942 e.g., the rotation disk could be "sandwiched" between two stationary disks. Regardless of the structure provided, the rotary adjustment of the location aperture 126' could be accomplished—whether or not a lateral slot 938 is present or utilized—through rotation of the rotation disk 940 with respect to the stationary disk(s) 942 until the location aperture 126' has achieved a desired position within the location ring 836. At least one set screw 944 (two shown in FIG. 8) could then be tightened, or another detent mechanism (not shown) activated, when provided, to hold the location aperture 126' firmly in the desired location-dictating position with respect to the remaining portions of the apparatus 100.

Through use of an appropriately configured lateral slot 938 and rotation disk 940 arrangement, the location aperture 126' can accordingly be placed at substantially any desired position upon the location structure 106', as opposed to being restricted to the grid of possible location aperture 126 positions in the location structure 106 shown in FIGS. 1A-1B. Accordingly, the location structure 106' shown in FIGS. 7-9 may allow for finer resolution in location choice than does the location structure 106 of FIG. 1A-1B.

Figure 9:
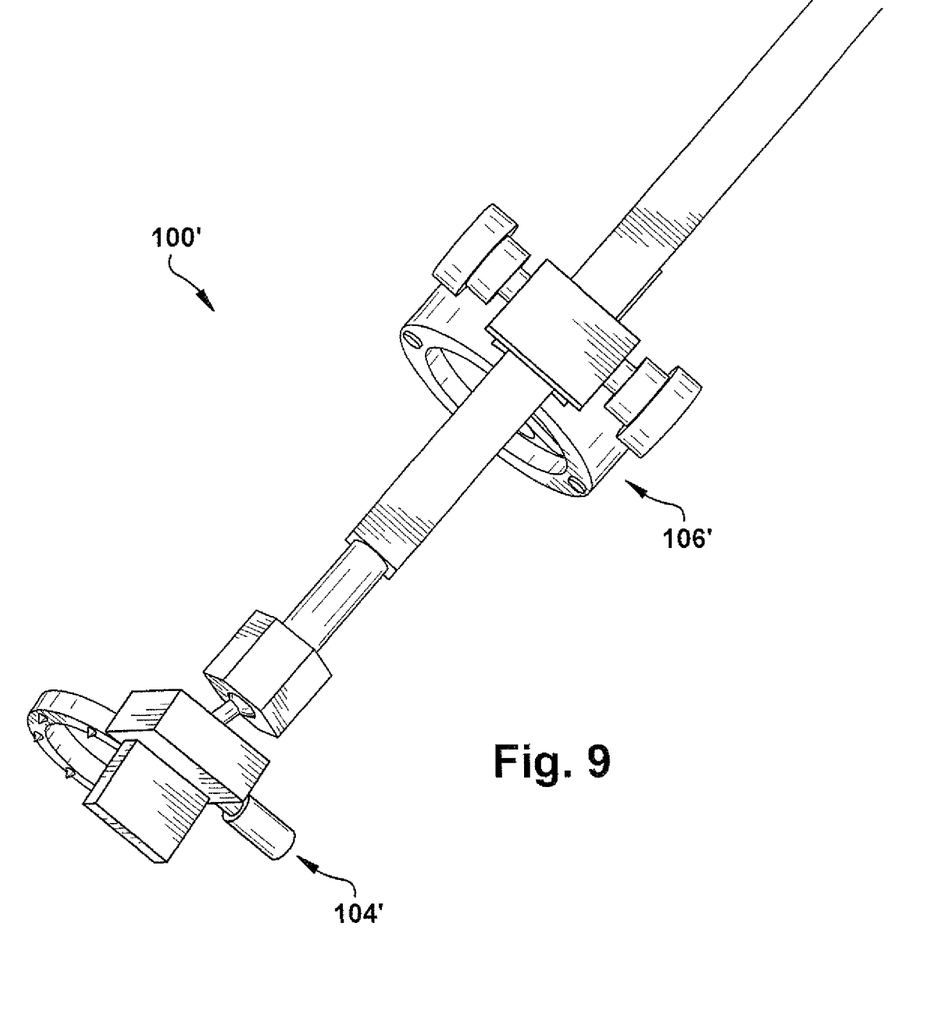
FIG. 9 is a partial rear perspective view of the embodiment of FIG. 7.

FIG. 9 is an additional view of the apparatus 100, showing another aspect of the optional configurations of the trajectory structure 104' and the location structure 106'.

Figure 10:
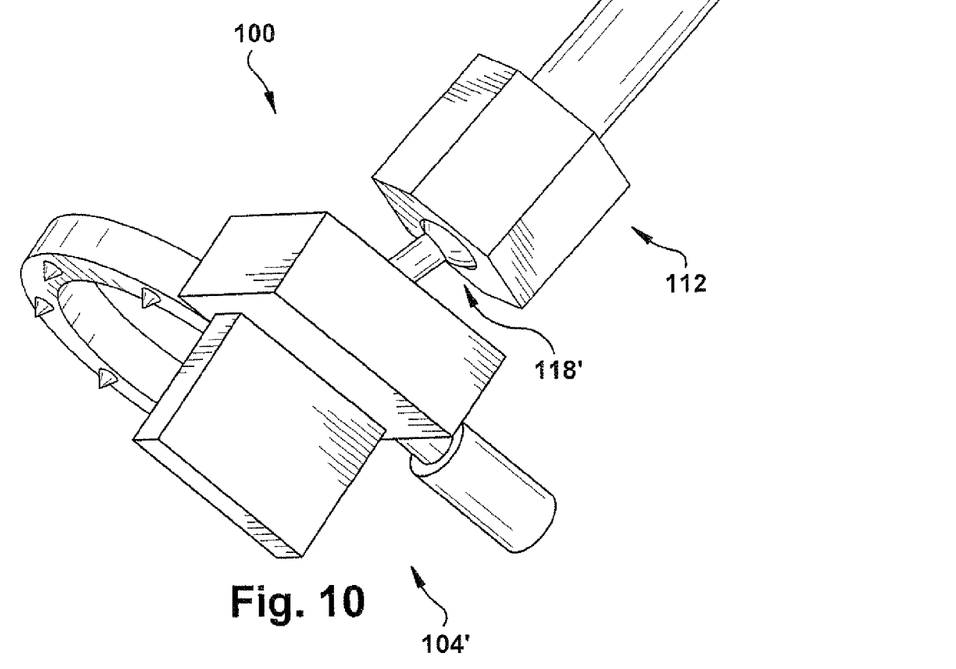
FIG. 10 is a partial rear perspective view of the embodiment of FIG. 7.

As shown in magnified view in FIG. 10, the trajectory structure 104' can be movably attached to the distal handling rod end 112 through the use of a wristed joint 118' of a ball-and-socket variety. (Positions of the ball and socket parts could be reversed from those shown.) No set screw is shown in FIG. 10 to tighten the wristed joint 118' and maintain the desired dictated trajectory because the ball-and-socket structure can be configured to have a fairly snug frictional fit and naturally resist movement from the set position. However, a set screw or other position maintenance aid structure could be provided for certain embodiments of the present invention.

Figure 11:
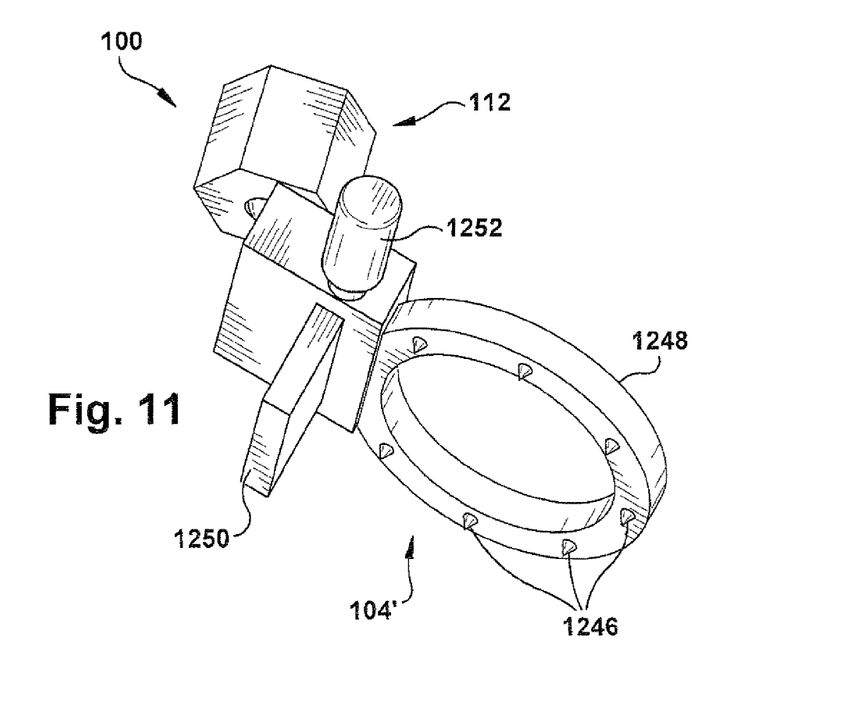
FIG. 11 is a partial bottom perspective view of the embodiment of FIG. 7.

FIG. 11 shows a magnified view of a portion of the apparatus 100, with a bottom portion of the trajectory structure 104' shown in detail. In FIG. 11, the trajectory structure 104' includes a plurality of anchoring spikes 1246 carried by a trajectory ring 1248. The anchoring spikes 1246 may be useful in maintaining a position of the trajectory ring 1248 on a surface 432 via friction and/or some degree of penetration into the surface, particularly if the surface is wet or slippery. While a plurality of relatively sharp, conical anchoring spikes 1246 are shown in the Figures, suitable anchoring spikes could have any configuration, number, location on the apparatus, or other physical characteristics. For example, the term "anchoring spikes" as used herein would also encompass a roughened area of the trajectory structure 104' which frictionally engages the surface 432.

FIG. 11 also shows a locating fin 1250 which may be either rigidly or movably attached to other structures of the trajectory structure 104'. As an example of movable attachment, the locating fin 1250 shown in FIG. 11 is permitted to pivot with respect to a plane of the trajectory ring 1248 and may be maintained in a desired pivotal position with respect to the trajectory ring by tightening of set screw 1252. The locating fin 1250, regardless of its actual physical configuration, may be configured to contact a preselected structure of an underlying surface 432 in order to help locate, steady, and/or maintain a position of the trajectory structure 104' or another portion of the apparatus 100 with respect to the underlying surface 432. For example, if the surface 432 is a glenoid surface of a scapula 430, the locating fin 1250 may be configured to contact the glenoid rim in a predetermined manner to more quickly and/or positively locate the trajectory structure 104' with respect to the glenoid surface than might be readily accomplished in the absence of the locating fin. The locating fin 1250, like all structures of the apparatus 100, may have a "generic" configuration allowing reuse with multiple patients, or may include patient specific features and be at least partially disposable/replaceable.

Figure 12:
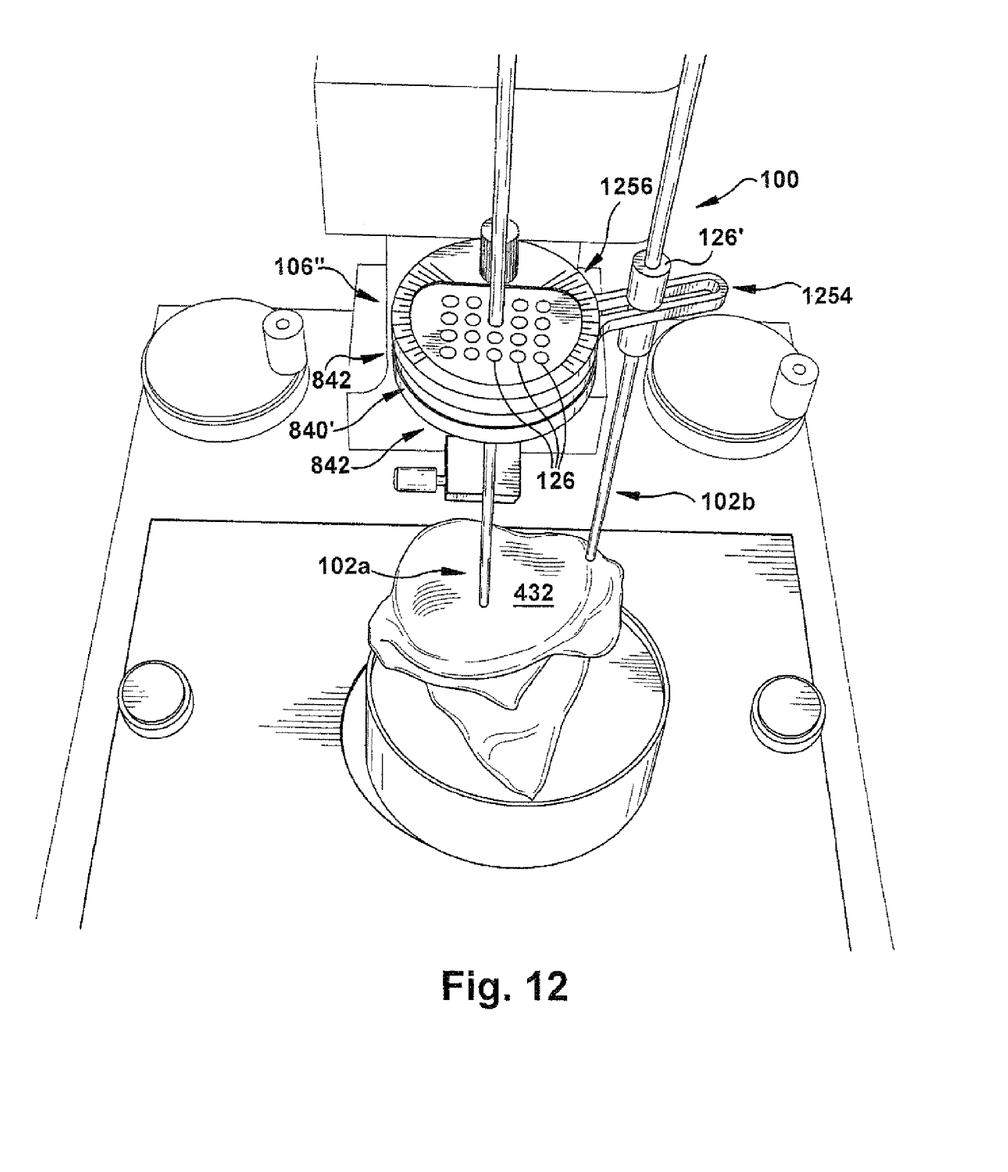
FIG. 12 is a top perspective view of the embodiment of FIG. 1A in an optional configuration.

In FIG. 12, another example configuration of the location structure 106" is shown. The apparatus 100 shown in partial view in FIG. 12 is configured to dictate the insertion trajectory/location of the first pin 102a and/or an additional pin 102b, with the additional pin being placed using a protruding arm 1254, which may be stationary or adjustable. The apparatus 100 of FIG. 12 may also or instead be used in conjunction with a previously placed additional pin 102b to help position the apparatus 100 with respect to the surface 432 such that the apparatus 100 dictates an insertion trajectory and/or location for the pin 102b placed using the location structure 106" and the trajectory structure (omitted from FIG. 12 for clarity).

The additional pin 102b can be used in conjunction with the adjustable protruding arm 1254 (shown here as including a cylindrical bushing configured to act as a location aperture 126' and accept the additional pin 102b). As shown in FIG. 12, the protruding arm 1254 may be movably connected to the remaining elements of the locating structure 106" through use of a rotation disk 840' which is "sandwiched" between two stationary disks 842 for operation, including optional tightening, in a similar manner to the rotation disk 840 described above with reference to FIGS. 7-9.

The rotation disk 840' can be pivoted to allow the protruding arm 1254 to extend laterally at different angles relative to the remaining portions of the locating structure 1054. Optionally, and as shown in FIG. 12, a rotational scale 1256 may be provided to assist with achieving a desired angular relationship between the protruding arm 1254 and other portions of the locating structure 106". Also optionally, a locking or detent mechanism (not shown) may be provided to help maintain the desired angular relationship between the protruding arm 1254 and other portions of the locating structure 106".

The cylindrical bushing location aperture 126' can be moved laterally with respect to (toward and away from) the grid of location apertures 126 formed in the central portion of the locating structure 106". Additionally, in the configuration shown in FIG. 12, the protruding arm 1254 can be rotated around the outer perimeter of the location structure 106" to allow rotary placement of the cylindrical bushing location aperture 126' in a variety of angular "yaw" positions with respect to the remaining portions of the location structure 106". Accordingly, using the apparatus 100 in FIG. 12, one pin 102a can be placed at a desired insertion trajectory and/or location at the same time that an additional pin 102b can be placed at a desired insertion trajectory and/or location. Optionally, either or both of the pins 102a and 102b could be pre-placed at an insertion trajectory and/or location, through any desired means, and then used to help place the apparatus 100 into a predetermined position, in a substantial reversal of the previously described use of the apparatus to place one or more pins.

While aspects of the present invention have been particularly shown and described with reference to the preferred embodiment above, it will be understood by those of ordinary skill in the art that various additional embodiments may be contemplated without departing from the spirit and scope of the present invention. For example, the apparatus or components thereof may be made of any suitable material or combination of materials, such as, but not limited to, stainless steel, aluminum, other metals, plastics, and ceramics. Instead of the depicted location apertures 126, the location structure 106 could include a single, relatively large longitudinal aperture (e.g., a structure akin to the location ring 836) through which the pin 102 is placed, optionally with a wire grid extending laterally across some portion of the aperture to assist in more precise positioning of the pin. The location apertures 126 could have different diameters to accommodate different sizes of pins 102, or could have non-circular borders to assist with orienting a pin for insertion. The trajectory structure 104 does not necessarily contact the surface 432 during insertion of the pin 102, although one of ordinary skill in the art will likely desire some mechanism for steadying the trajectory structure relative to the surface if no contact exists therebetween. The pin 102 could be inserted wholly into the surface 432, with no protruding portions, particularly if the pin is a therapeutic pin and intended for at least semi-permanent dwelling in the surface 432 or underlying structures. The specific methods described above for using the described system are merely illustrative; one of ordinary skill in the art could readily determine any number of devices, sequences of steps, or other means/options for dictating the insertion trajectory and/or location as described. Any of the described structures and components could be integrally formed as a single piece or made up of separate sub-components, with either of these formations involving any suitable stock or bespoke components and/or any suitable material or combinations of materials. It is contemplated that the apparatus 100 may be reusable (optionally sterilizable), though portions or the whole thereof may be disposable. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A variety of schemes are described herein for placing the apparatus 100 into the predetermined dictation configuration, and these schemes can be used singly or in any suitable combination for a particular application of the present invention. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, We claim:

1. An apparatus for dictating trajectory and location for insertion of an elongate pin into a surface, the apparatus comprising:
    a trajectory structure configured for contact with the surface to dictate an insertion trajectory of the pin relative to the surface;
    a location structure configured to allow longitudinal passage of at least a portion of the pin therethrough to dictate an insertion location of the pin relative to the surface; and
    an elongate handling rod connected to the trajectory structure and the location structure and supporting the trajectory structure and the location structure for manipulation by a user;
    wherein the handling rod spaces the trajectory structure and the location structure longitudinally apart, the entirety of the trajectory structure is connected to the handling rod via a single, wristed joint located directly adjacent the trajectory structure for trajectory adjustment in at least two degrees of freedom relative to the handling rod, and the insertion trajectory of the pin insertion is substantially dependent upon the trajectory adjustment.

2. The apparatus of claim 1, wherein the location structure includes an adjustable location aperture which is movable within a location ring, and the insertion location is at least partially dictated by the position of the location aperture with respect to the location ring.

3. The apparatus of claim 2, wherein the location aperture is laterally movable along a lateral slot within the location ring to set the position of the location aperture with respect to the location ring.

4. The apparatus of claim 2, wherein the location aperture is carried by a rotation disk which makes the location aperture rotatable within the location ring to set the position of the location aperture with respect to the location ring.

5. The apparatus of claim 1, wherein the location structure includes an adjustable location aperture which is movable within a location ring, the location aperture extends substantially perpendicular to a lateral plane defined by the location ring and is substantially infinitely adjustable within an area of the lateral plane defined by the location ring which is bounded by the structure of the location ring to achieve a position of the location aperture which is not restricted to a grid of possible location aperture positions, and the insertion location is at least partially dictated by the position of the location aperture with respect to the location ring.

6. The apparatus of claim 1, wherein the trajectory structure includes at least one anchoring spike protruding therefrom and configured to maintain a position of the trajectory structure in contact with the surface using at least one of frictional and penetrating engagement.

7. The apparatus of claim 1, wherein the trajectory structure includes at least one locating fin protruding therefrom, the locating fin contacting a preselected structure of the surface to assist with at least one of location, steadying, and maintaining the trajectory structure in a predetermined position with respect to the surface.

8. The apparatus of claim 7, wherein the locating fin is movably attached to at least one other structure of the trajectory structure.

9. The apparatus of claim 1, wherein the pin is a first pin, and the location structure includes a protruding arm extending therefrom, a location aperture of the protruding arm dictating at least one of an insertion trajectory and an insertion location of a second pin relative to the surface.

10. The apparatus of claim 9, wherein the location aperture of the protruding arm is laterally movable relative to at least one remaining portion of the location structure to set the position of the location aperture with respect to the remaining portion of the location structure.

11. The apparatus of claim 9, wherein the location aperture of the protruding arm is rotatably movable relative to at least one remaining portion of the location structure to set the position of the location aperture with respect to the remaining portion of the location structure.

12. The apparatus of claim 1, wherein at least one of the insertion trajectory and the insertion location is chosen to provide a desired guide pin location determined with reference to a multi-dimensional image of the surface.

13. The apparatus of claim 1, wherein the angle of the handling rod relative to the trajectory structure at a location adjacent the trajectory structure directly corresponds to the insertion trajectory.

14. The apparatus of claim 1, wherein the apparatus only contacts an area of the surface directly adjacent the insertion location.

15. The apparatus of claim 1, wherein an entirety of the trajectory structure is longitudinally interposed between an entirety of the location structure and the surface when the insertion location and insertion trajectory of the pin relative to the surface is being dictated.

\* \* \* \* \*